(12) United States Patent
Reiter et al.

(10) Patent No.: US 7,294,701 B2
(45) Date of Patent: Nov. 13, 2007

(54) ANTIBODY FRAGMENT CAPABLE OF MODULATING MULTIDRUG RESISTANCE AND COMPOSITIONS AND KITS AND METHODS USING SAME

(75) Inventors: Yoram Reiter, Haifa (IL); Maya Haus-Cohen, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 480 days.

(21) Appl. No.: 10/405,123

(22) Filed: Apr. 2, 2003

(65) Prior Publication Data

US 2004/0197334 A1    Oct. 7, 2004

(51) Int. Cl.
*C07K 16/30* (2006.01)
(52) U.S. Cl. .............................. 530/387.1; 530/387.7; 530/387.9
(58) Field of Classification Search ............. 530/387.1, 530/387.7, 387.9
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,752 A | 11/1974 | Schuurs et al. | |
| 3,853,987 A | 12/1974 | Dreyer | |
| 3,867,517 A | 2/1975 | Ling | |
| 3,879,517 A | 4/1975 | Meyn et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,666,828 A | 5/1987 | Gusella | |
| 4,683,202 A | 7/1987 | Mullis | |
| 4,801,531 A | 1/1989 | Frossard | |
| 4,837,306 A | 6/1989 | Ling et al. | |
| 4,866,042 A | 9/1989 | Neuwelt | |
| 4,879,219 A | 11/1989 | Wands et al. | |
| 5,011,771 A | 4/1991 | Bellet | |
| 5,192,659 A | 3/1993 | Simons | |
| 5,223,409 A | 6/1993 | Ladner et al. | |
| 5,272,057 A | 12/1993 | Smulson et al. | |
| 5,281,521 A | 1/1994 | Trojanowski | |
| 5,403,484 A | 4/1995 | Ladner et al. | |
| 5,403,574 A | 4/1995 | Piwnica-Worms | |
| 5,427,908 A | 6/1995 | Dower et al. | |
| 5,434,075 A * | 7/1995 | Mechetner et al. ......... 435/328 |
| 5,464,764 A | 11/1995 | Capecchi | |
| 5,487,992 A | 1/1996 | Capecchi | |
| 5,516,637 A | 5/1996 | Huang et al. | |
| 5,543,423 A | 8/1996 | Zelle et al. | |
| 5,556,856 A | 9/1996 | Engel et al. | |
| 5,571,698 A | 11/1996 | Ladner et al. | |
| 5,580,717 A | 12/1996 | Dower et al. | |
| 5,658,727 A | 8/1997 | Barbas et al. | |
| 5,698,426 A | 12/1997 | Huse | |
| 5,733,743 A | 3/1998 | Johnson et al. | |
| 5,750,753 A | 5/1998 | Kimae et al. | |
| 5,766,946 A | 6/1998 | Cianfriglia | |
| 5,780,225 A | 7/1998 | Wigler et al. | |
| 5,821,047 A | 10/1998 | Garrard et al. | |
| 5,932,447 A | 8/1999 | Siegall | |
| 5,969,108 A | 10/1999 | McCafferty et al. | |
| 6,479,639 B1 * | 11/2002 | Metchetner et al. ..... 530/387.9 |

FOREIGN PATENT DOCUMENTS

WO        94/10198      *  5/1994

OTHER PUBLICATIONS

Mayforth Designing Antibodies, Academic Press p. 106-107 (1993).*
Niv et al Int. J. Cancer vol. 94 p. 864-872 (2001).*
Roninson et al. "Amplification Of Specific DNA Sequences Correlates With Multi-Drug Resistance in Chineses Hamster Cells", Nature, 309: 626-628, 1984.
Goldstein et al. "Expression of a Multidrug Resistance Gene in Human Cancers", Journal of the National Cancer Institute, 81: 116-124, 1989.
Tsuruo et al. "Overcoming of Vincristine Resistance in P388 Leukemia In Vivo and In Vitro Through Enhanced Cytotoxicity of Vincristine and Vinblastine by Verapamil", Cancer Res., 41: 1967-1972, 1981.
Hamada et al. "Functional Role for the 170- to 180-kDa Glycoprotein Specific to Drug-Resistant Tumor Cells as Revealed By Monoclonal Antibodies", Proc. Natl. Acad. Sci. USA, 83: 7785-7789, 1986.
Jain "Delivery of Molecular Medicine to Solid Tumors", Science, 271:1079-1080, 1996.
Huston et al. "Protein Engineering of Antibody Binding Sites: Recovery of Specific Activity in an Anti-Digoxin Single-Chain Fv. Analogue Produced in *Escherichia coli*.", Proc. Natl. Acad. Sci. USA 85: 5879-5883, 1996.
Hoogenboom et al. "Multi-Subunit Proteins On The Surface Of Filamentous Phage: Methodologies For Displaying Antibody (Fab) Heavy And Light Chains",Nucleic Acids Research, 19(15): 4133-4137, 1991.

(Continued)

*Primary Examiner*—Sheela J. Huff

(57) ABSTRACT

An antibody fragment and methods of utilizing same are provided. The antibody fragment includes an antigen binding region capable of binding an extracellular portion of a P-glycoprotein thereby at least partially inhibiting drug efflux activity in multidrug resistant cells.

1 Claim, 5 Drawing Sheets

OTHER PUBLICATIONS

Eva et al. "Cellular Genes Analogous to Retroviral onc Genes are Transcribed in Human Tumour Cells", Nature, 295: 116-119, 1982.

Denkberg et al. "Direct Visualization of Distinct T Cell Epitopes Derived from a Melanoma Tumor-Associated Antigen by Using Human Recombinant Antibodies with MHC-Restricted T Cell Receptor-Like Specificity", Proc. Natl. Acad. Sci., 99(14): 9421-9426, 2002.

Akiyama et al. "Isolation and Genetic Characterization of Human KB Cell Lines Resistant to Multiple Drugs", Somaic Cell and Molecular Genetics 11(2): 117-126, 1985.

Sharma et al. "A Phenotype Conferring Selective Resistance to Lipophilic Antifolates in Chinese Hamster Oval Cells", Cancer Res., 51: 2949-2959, 1991.

Brisson et al. "Expresion Of A Bacterial Gene In Plants By Using A Viral Vector", Nature, 310:511-514, 1984.

Brogli et al. "Light-Regulated Expression Of A Pea Ribulose-1,5-Bisphosphate Carboxylase Small Subunit Gene In Transformed Plant Cells", Science, 224 :838-843, 1984.

Cinciarelli et al. "Characterization By Somatic Cell Genetics Of A Monoclonal Antibody To The MDR1 Gene Product (P-Glycoprotein): Determination Of P-Glycoprotein Expression In Multi-Drug-Resistant KB And CEM Cell Variants", Int. J. Cancer, 47:533-543, 1991.

Clackson et al., "Making Antibody Fragments using Phage Display Libraries", Nature, 352: 624-628, 1991.

Cole et al. "Pharmcological Characterization Of Multidrug Resistant MRP-Transfected Human T%umor Cells", Cancer Research, 54: 5902-5910, 1994.

Gurley et al. "Upstream Sequences Required For Efficient Expression Of A Soybean Heat shock Gene". Molecular and Cellular Biology, 6(2): 559-565, 1986.

Hamada et al. "Mouse-Human Chimeric Antibody Against The Multidrug Transporter P-Glycoprotein", Cancer Research, 50: 3167-3171, 1990.

Lej et al. "Charcterization Of The Erwinia Carotovora PelB Gene And Its Product Pectate Lyase", Journal of Bacteriology, 169(9): 4379-4383, 1987.

Meyers et al. "Characterization Of Monoclonal Antibodies Recognizing A Mr 180,000 P-Glycoprotein: Differntial Expression Of the Mr 180,000 and Mr170,000 P-Glycoproteins In Multidrug-Resistant Human Tumor Cells", Cancer Research, 49:3209-3214, 1989.

Pearson et al. "Reversal Of Drug Resistance In A Human Colon Cancer Xenograft Expressionb MDR1 Complementary DNA By In Vivo Administation Of MRK-16 Monoclonal Antibody", Journal of the National Cancer Institute, 83(19):1386-1391, 1991.

Takamutsu et al. "Expression Of Bacterial Chloramphenicol Acetyltransferase Gene In Tobacco Plants Mediated By TMV-RNA", EMBO Journal, 6(2): 307-311, 1987.

Coruzzi et al. "Tissue-Specific And Light-Regulated Expression Of A Pea Nuclear Gene Encoding The Small Subunit of Ribulose-1,5-Bisphosphate Carboxylase", EMBO Journal; 3(8):1671-1680, 1984.

von Heijne "Signal Sequences The Limits Of Variation",Journal of Molecular Biology, 184: 99-105, 1985.

Yakota et al. "Rapid Tumor Penetration Of A Single-Chain Fv And Comparison With Other Immunoglobulin Forms", Cancer Res., 52:3402-3408, 1992.

* cited by examiner

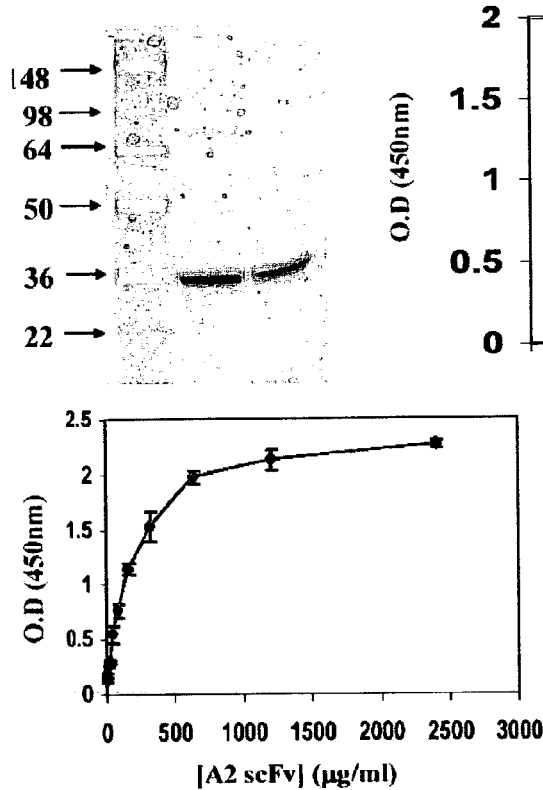
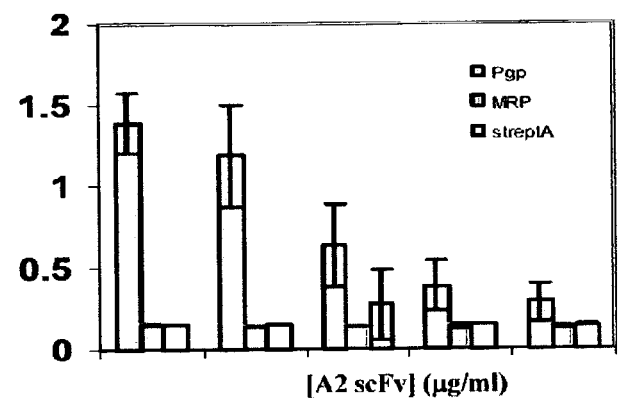
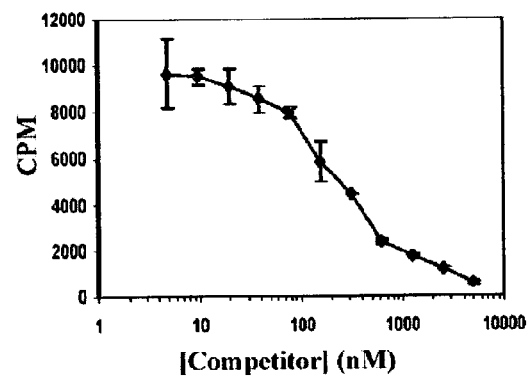
Fig. 1a  Fig. 1b
Fig. 1c  Fig. 1d

Fig. 2a
2780
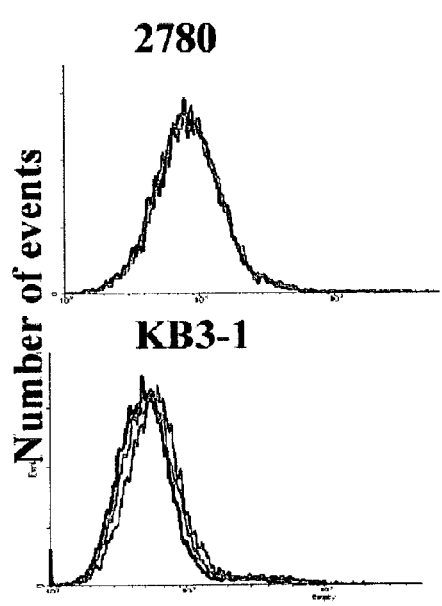
Fig. 2b
2780$^{ADR}$
A2 scFv
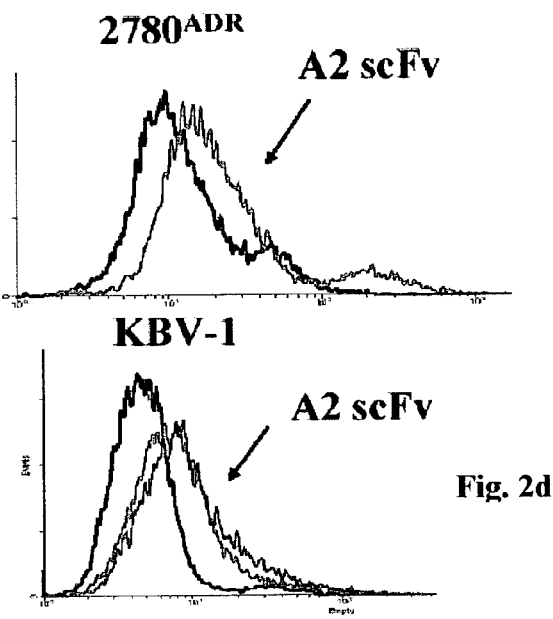
KB3-1
KBV-1
A2 scFv
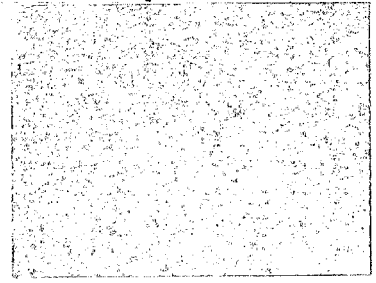
Fig. 2d
Fig. 2c
Fluorescence intensity
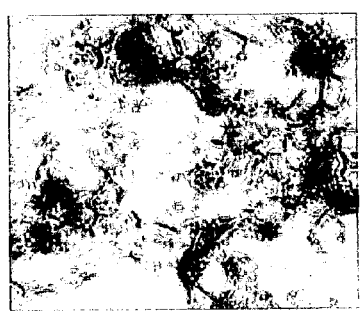
Fig. 2e
Fig. 2f
Fig. 2g
Fig. 2h Fig. 3a
Fig. 3b
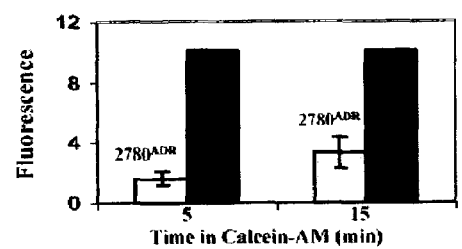
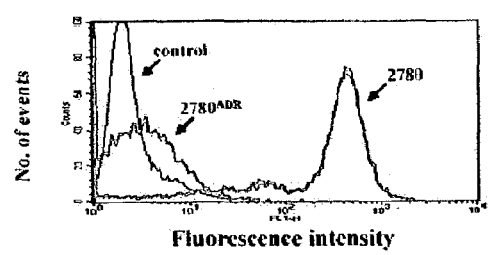
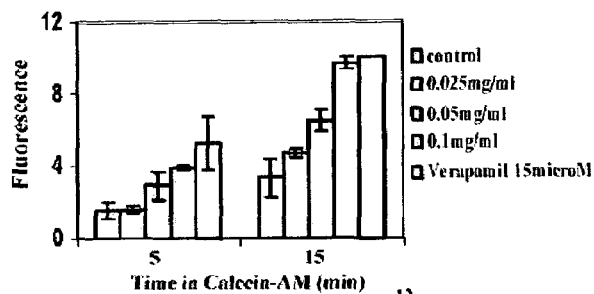
Fig. 3c
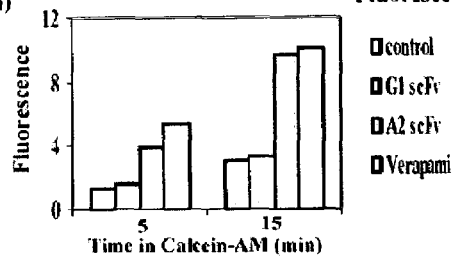
Fig. 3d
Fig. 3e Fig. 5
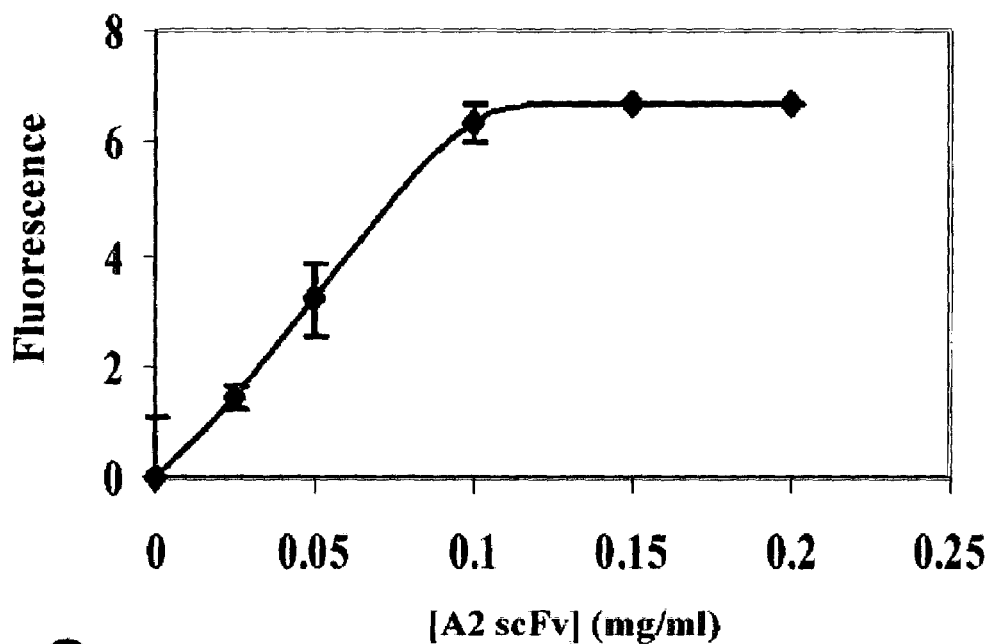
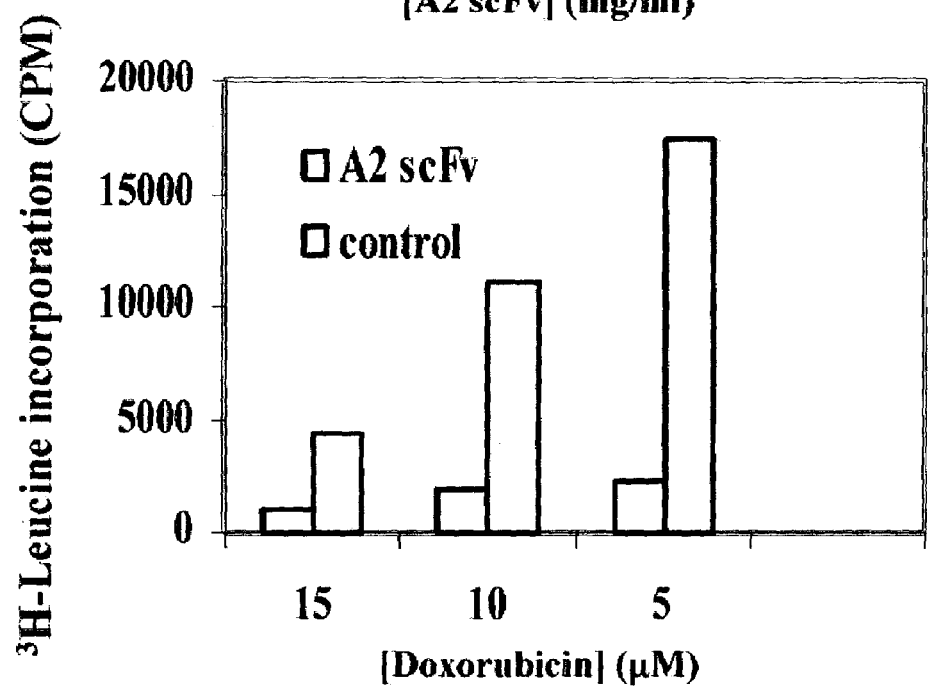
Fig. 6

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial sequence
<220> FEATURE:
<223> OTHER INFORMATION: Multidrug resistance protein 1 (MDR1) derived
      peptide

<400> SEQUENCE: 1

Gly Glu Met Thr Asp Ile Phe Ala Asn Ala Gly Asn Leu
1               5                   10

<210> SEQ ID NO 2
<211> LENGTH: 723
<212> TYPE: DNA
<213> ORGANISM: Artificial sequence
<220> FEATURE:
<223> OTHER INFORMATION: A2 single chain Fv coding sequence

<400> SEQUENCE: 2
caggtccaac tgcagcagtc tggacctgac ctggtgaagc tgggggcttc agtgaagata      60
tcctgcaagg cttctggtta ctcattcact ggctactaca tgcactgggt gaagcagagc     120
catggaaaga gccttgagtg gattggacgt gctaatccta caaatggtgg tactagctac    180
```

```
aaccagaagt tcaagggcaa ggccatatta actgtagaca agtcatccag cacagcctac    240
atggagctcc gcagcctgac atctgaggac tctgcagtct attactgtgc aagatgggac    300
ggggcttact ggggccaagg gactctggtc actgtctctt cgggaggtgg tggatccggc    360
ggtggcggtt ctggtggagg tggatctgat gttgtgatga cccaaactcc actctccctg    420
cctgtcagtc ttggagatca agcctccatc tcttgcagat ctagtcagag cattgtacat    480
agtaatggaa acacctattt agaatggtac ctgcagaaac caggccagtc tccaaagctc    540
ctgatctaca aagtttccaa ccgatttcct ggggtcccag acaggttcag tggcagtgga    600
tcagggacag atttcacact caagatcagc agagtggagg ctgaggatct gggagtttat    660
tactgctttc aaggttcaca tgttccattc acgttcggct cggggaccaa gctggaactg    720
aaa                                                                  723

<210> SEQ ID NO 3
<211> LENGTH: 33
<212> TYPE: DNA
<213> ORGANISM: Artificial sequence
<220> FEATURE:
<223> OTHER INFORMATION: Myc-tag coding sequence

<400> SEQUENCE: 3
gaacaaaaac tcatctcaga agaggatctg aat                                 33
```

ANTIBODY FRAGMENT CAPABLE OF MODULATING MULTIDRUG RESISTANCE AND COMPOSITIONS AND KITS AND METHODS USING SAME

FIELD AND BACKGROUND OF THE INVENTION

The present invention relates to an antibody fragment capable of binding to P-glycoprotein associated with multidrug resistant (MDR) cells. The present invention also relates to compositions and methods utilizing such an antibody fragment for inhibiting drug efflux activity in MDR cancer cells.

Cancer chemotherapy often fails due to the development of acquired or intrinsic resistance in cancerous cells to a wide variety of anticancer drugs, such as colchicine, vinblastine, vincristine and doxorubicin. This phenomenon, which is known as multidrug resistance (MDR), is a major barrier to cancer chemotherapy.

A key mechanism of MDR is the overexpression of an energy-dependant efflux pump, known as the multidrug transporter. This efflux pump is a 170 kDa P-glycoprotein (Pgp), encoded by the MDR1 gene. Pgp-mediated MDR plays an important role in the resistance of various tumor cells to chemotherapy; studies have shown a clear correlation between mdr1 expression and the lack of response to chemotherapy (6,7).

Inhibitors of the MDR phenotype in cancer cells may either modify or disrupt the expression of the drug efflux function of the transporter proteins involved in MDR. Known MDR inhibitors include verpamil (a calcium-channel blocker and being used to treat leukemia), cyclosporins, steroids, and calmodulin inhibitors (which enhance the intracellular accumulation and cytotoxic action of Pgp-transported drugs). However, most known MDR-modulating drugs presently available for clinical application have major side effects which substantially limit their therapeutic value.

Recently, Pgp-specific monoclonal antibodies (Mab) have been developed as intended agents for use in MDR inhibition. U.S. Pat. No. 4,837,306 describes antibodies directed against the C-terminal portion of the intracellular domain of Pgp. These antibodies are not known to have an inhibitory effect on the drug efflux activity in MDR cells.

U.S. Pat. No. 5,766,946 describes a monoclonal antibody termed MM.17 that recognizes an epitope located on the forth extracellular loop of human Pgp. The MM.17 antibody was generated by immunizing mice with an MDR variant of a human T-lymphoblastoid. This antibody is not known to have an inhibitory effect on the drug efflux activity in MDR cells.

U.S. Pat. No. 6,479,639 describes a monoclonal antibody termed UIC2 directed against an extracellular domain of Pgp. The UIC2 antibody was generated by immunizing mice with transfected fibroblast cells expressing Pgp. The UIC2 Mab was found capable of inhibiting the drug efflux activity of MDR cells in vitro.

Monoclonal antibodies termed HYB-241 and HYB-612, recognize an external epitope of Pgp. These Mabs have been reported to increase the accumulation of the chemotherapeutic drugs vincristine and actinomycin D in tumor cells thereby increasing cytotoxicity [Meyers, M. B. et al., Cancer Res., 49:3209 (1987); O'Brien, J. P. et al., Proc. Amer. Assoc. Cancer Res., 30:Abs 2114 (1989)].

The monoclonal antibody Mab657 has been reported to react with MDR cells [Cinciarelli, C., et al., Int. J. Cancer, 47:533 (1991)]. This antibody was reported to increase the susceptibility of MDR cells to cytotoxicity mediated by human peripheral blood lymphocytes, it is not known to have an inhibitory effect on the drug efflux activity of Pgp.

The monoclonal antibodies MRK-16 and MRK-17, were generated by immunizing mice with MDR human leukemia cells. Both antibodies recognize Pgp and are capable of modulated the drug efflux activity in MDR cells MDR in vitro and in vivo [Hamada H., et al., Cancer Res. PNAS 83:7785 (1986); Pearson, J. W., et al., J. Natl. Cancer Inst. 88:1386 (1991); Tsuruo, T., et. al., Jpn. J. Cancer Res. 80:627 (1989)]. A recombinant chimeric antibody that combines the variable region of MRK-16 with the Fc portion of human antibodies was reported to be more effective than parent MRK-16 Mab in increasing cytotoxicity to MDR cells in vitro [Hamada H. et al., cancer Res. 50:3167 (1990)].

A substantial limitation of the above described antibodies stems from the large size of these molecules. It is well known that delivery efficiency of an agent is typically inversely proportional to its size. Thus, the large antibody molecules described above would not efficiently penetrate and distribute within the tumor tissue requiring high administration dosages to obtain therapeutic effect.

Another major shortcoming of presently available Pgp-specific antibodies is the fact that Pgp is constitutively expressed in normal human tissues, including kidney, liver, colon, testis, lymphocytes, and the blood-brain barrier (27). A large antibody molecule would typically circulate for extended time periods and would be slowly cleared from circulation resulting in possible toxic effects on normal tissues that physiologically express Pgp.

In addition, most of the Pgp-specific antibodies described above were selected for high affinity to Pgp. However, the practical use of Pgp-specific antibodies in therapy may be substantially restricted when the binding affinity of the antibody to Pgp is high. This is due to toxic effects that might be exerted on normal tissues that physiologically express Pgp.

There is thus a widely recognized need for, and it would be highly advantageous to have, a Pgp-specific antibody devoid of the above limitations.

SUMMARY OF THE INVENTION

According to one aspect of the present invention there is provided an antibody fragment comprising an antigen binding region capable of binding an extracellular portion of a P-glycoprotein, wherein the antibody fragment is capable of at least partially inhibiting drug efflux activity in multidrug resistant cells.

According to another aspect of the present invention there is provided a pharmaceutical composition, comprising, as an active ingredient, an antibody fragment including an antigen binding region capable of binding an extracellular portion of a P-glycoprotein, wherein the antibody fragment is capable of at least partially inhibiting drug efflux activity in multidrug resistant cells and a pharmaceutically acceptable carrier.

According to yet another aspect of the present invention there is provided a method of treating cancer in an individual, comprising: (a) providing to the individual an antibody fragment capable of at least partially inhibiting drug efflux activity in multidrug resistant cancer cells, and (b) administrating to the individual a therapeutically effective amount of an anti cancer agent thereby treating cancer in the individual.

According to still another aspect of the present invention there is provided a kit for diagnosing cells overexpressing P-glycoprotein, comprising an antibody fragment containing an antigen binding region capable of binding said P-glycoprotein, and reagents for detecting said antibody fragment.

According to an additional aspect of the present invention there is provided a method of detecting cells overexpressing P-glycoprotein comprising: (a) exposing the cells to an antibody fragment including an antigen binding region capable of binding an extracellular portion of the P-glycoprotein; and (b) detecting said antibody fragment bound to said extracellular portion of said P-glycoprotein, thereby identifying the cells overexpressing extracellular P-glycoprotein.

According to yet an additional aspect of the present invention there is provided an isolated polynucleotide comprising a nucleic acid sequence encoding an antibody fragment including an antigen binding region capable of binding an extracellular portion of a P-glycoprotein, wherein the antibody fragment is capable of at least partially inhibiting drug efflux activity in multidrug resistant cells.

According to still an additional aspect of the present invention there is provided a nucleic acid construct comprising an isolated polynucleotide which includes a nucleic acid sequence encoding an antibody fragment including an antigen binding region capable of binding an extracellular portion of a P-glycoprotein, wherein the antibody fragment is capable of at least partially inhibiting drug efflux activity in multidrug resistant cells.

According to a further aspect of the present invention there is provided a cell comprising a nucleic acid construct which includes an isolated polynucleotide comprising a nucleic acid sequence encoding an antibody fragment including an antigen binding region capable of binding an extracellular portion of a P-glycoprotein, wherein the antibody fragment is capable of at least partially inhibiting drug efflux activity in multidrug resistant cells.

According to further features in preferred embodiments of the invention described below, the antibody fragment of the present invention is an Fv fragment, preferably a single chain Fv.

According to still further features in the described preferred embodiments the antibody fragment of the present invention is a Fab.

According to still further features in the described preferred embodiments the antibody fragment of the present invention is a F(ab')$_2$.

According to still further features in the described preferred embodiments the antibody fragment of the present invention is a F(ab')$_2$.

According to still further features in the described preferred embodiments the antibody fragment of the present invention includes an antigen binding region capable of binding an extracellular portion of a 170 kDa polypeptide expressed by the mdr1 gene, preferably the antigen binding region is directed against an epitope located in a first loop of the extracellular portion of the P-glycoprotein, more preferably the epitope comprises the amino acid sequence set forth in SEQ ID NO:1.

According to still further features in the described preferred embodiments the antibody fragment of the present invention is capable of at least partially inhibiting drug efflux activity in multidrug resistant cancer cells, preferably human cancer cells.

According to still further features in the described preferred embodiments the pharmaceutical composition of the present invention further includes a chemotherapeutic drug, preferably a chemotherapeutic drug which is toxic to cancer cells.

According to still further features in the described preferred embodiments the method of treating cancer in an individual includes providing to the individual an antibody fragment capable of at least partially inhibiting drug efflux activity in multidrug resistant cancer cells being administered along with a pharmaceutically acceptable carrier.

According to still further features in the described preferred embodiments the method of treating cancer in an individual includes administrating to the individual a therapeutically effective amount of an anti cancer agent prior to, concomitant with or following providing to the individual an antibody fragment capable of at least partially inhibiting drug efflux activity in multidrug resistant cancer cells.

According to still further features in the described preferred embodiments the method of treating cancer in an individual includes administrating to the individual a therapeutically effective amount of an anti cancer agent which is complexed with the antibody fragment of the present invention.

According to still further features in the described preferred embodiments the method of treating cancer in an individual includes expressing the antibody fragment of this invention within cells of the individual.

According to still further features in the described preferred embodiments the kit of the present invention further includes packaging material identifying the antibody fragment for use in diagnosing cells overexpressing extracellular P-glycoprotein.

According to still further features in the described preferred embodiments the kit of the present invention includes the antibody fragment of the present invention labeled with a detectable moiety, preferably the detectable moiety is selected from the group consisting of a chromogenic moiety, a fluorogenic moiety, a light-emitting moiety and a radioactive moiety.

According to still further features in the described preferred embodiments the method of detecting cells of an individual overexpressing P-glycoprotein further comprising obtaining a biological sample from the individual prior to exposing the cells to the antibody fragment of the present invention.

According to still further features in the described preferred embodiments the method of detecting cells overexpressing P-glycoprotein includes exposing the cells to the antibody fragment of the present invention which is labeled with a detectable moiety, preferably the detectable moiety is selected from the group consisting of a chromogenic moiety, a fluorogenic moiety, a light-emitting moiety and a radioactive moiety.

According to still further features in the described preferred embodiments the isolated polynucleotide of the present invention is as set forth in SEQ ID NO:2.

According to still further features in the described preferred embodiments the nucleic acid construct of the present invention further includes a promoter for regulating expression of said polynucleotide.

The present invention successfully addresses the shortcomings of the presently known configurations by providing an antibody fragment, a pharmaceutical composition, a polynucleotide, a nucleic acid construct, a kit and methods of utilizing same. The antibody fragment includes an antigen binding region capable of binding an extracellular portion of a P-glycoprotein thereby at least partially inhibiting drug efflux activity in multidrug resistant cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-d demonstrate specificity and binding properties of purified A2 single-chain Fv (scFv). FIG. 1a is a photograph of SDS-PAGE analysis presenting a single band of A2 scFv in the center and right lanes, while the left lane shows bands of molecular size standards. FIG. 1b is a bar graph of an ELISA of A2 scFv binding to biotinylated target Pgp-derived peptide (comprising an amino acid sequence of SEQ ID NO:1; Pgp), or to biotinylated non-target peptide (PRP), or to streptavidin (streptA). The graph shows that A2 scFv reacted with the target Pgp-derived peptide in a dose-dependant fashion. A2 scFv did not react with the non-target peptide or with streptavidin. FIG. 1c is a plot of an ELISA presenting a dose-response curve of binding of A2 scFv to a biotinylated target Pgp-derived peptide. The concentration of A2 scFv required for 50% binding was interpolated as ca. 150 nM. FIG. 1d is a competition radioimmunoassay plot. The plot is based on using a constant amount of [$^{125}$I]-labeled A2 scFv and an increasing amount of non-labeled A2 scFv (as a competitor). The required concentration for 50% binding inhibition of A2 scFv was interpolated as ca. 130 nM.

FIGS. 2a-h demonstrate the capacity and selectivity of A2 scFv binding to tumor cells exhibiting multi-drug resistant (MDR) and over-expressing P-glycoprotein (Pgp). FIG. 2a is a plot presenting an immunofluorescence flow-cytometer analysis of A2 scFv reacting with drug-sensitive human ovarian carcinoma cells 2780. The plot shows that A2 scFv treatment had no effect on fluorescent intensity, indicating no antibody-cell binding. FIG. 2b is a plot presenting an immunofluorescence flow-cytometer analysis of A2 scFv reacting with MDR and Pgp-overexpressing ovarian carcinoma cells $2780^{ADR}$. The plot shows that A2 scFv treatment resulted in a 10-fold increase in fluorescent intensity, indicating strong antibody-cell binding. FIG. 2c is a plot presenting an immunofluorescence flow-cytometer analysis of A2 scFv reacting with drug-sensitive human carcinoma cells KB3-1. The plot shows that A2 scFv treatment had no effect on fluorescent intensity, indicating no antibody-cell binding. FIG. 2d is a plot presenting an immunofluorescence flow-cytometer analysis of A2 scFv reacting with MDR and Pgp-overexpressing human carcinoma cells KBV-1 (derived from the drug-sensitive human carcinoma cells KB3-1). The plot shows that A2 scFv treatment resulted in a substantial increase in fluorescence intensity, indicating a strong antibody-cell binding. FIG. 2e is a microphotograph illustrating immuno-histochemical staining of MDR and Pgp-overexpressing ovarian carcinoma cells $2780^{ADR}$ (derived from the drug-sensitive ovarian carcinoma cell line 2780), treated with A2 scFv. The microphotograph shows stained cells indicating a positive antibody-cell reaction. FIG. 2f is a microphotograph illustrating immuno-histochemical staining of drug-sensitive cells 2780 treated with A2 scFv. Cells were remained unstained indicating no antibody-cell reaction. FIG. 2g is a microphotograph illustrating immuno-histochemical staining of MDR and Pgp-overexpressing human carcinoma cells KB3-1 (derived from drug sensitive human carcinoma cell line KBV-1) treated with A2 scFv. The microphotograph shows stained cells indicating a positive antibody-cell reaction. FIG. 2h is a microphotograph illustrating immuno-histochemical staining of drug sensitive human carcinoma cells KBV-1 (the parent line of the MDR and Pgp-overexpressing human carcinoma cell line KB3-1) treated with A2 scFv. Cells were remained unstained indicating no antibody-cell reaction.

FIGS. 3a-e demonstrate the effect of A2 scFv on drug efflux activity in MDR cells. FIG. 3a is a bar graph presenting data obtained by a fluorometer assay comparing the calcein accumulation rate in (i) drug-sensitive human ovarian carcinoma cells 2780 (represented by black bars), and in (ii) MDR and Pgp-overexpressing ovarian carcinoma cells $2780^{ADR}$ (represented by gray bars). The graph shows 5 and 10-fold decrease in fluorescence intensity, indicating a decrease in calcein uptake, after 5 or 15 min incubation, respectively. FIG. 3b is a plot presenting a flow cytometer assay comparing calcein accumulation in (i) drug-sensitive human ovarian carcinoma cells 2780, and in (ii) MDR and Pgp-overexpressing human ovarian carcinoma cells $2780^{ADR}$. The plot shows that the $2780^{ADR}$ cells exhibited substantially lower mean fluorescence intensity, indicating a substantially lower level of calcein uptake by the MDR cells, as compared with the calcein uptake by the drug-sensitive 2780 cells. FIG. 3c is a bar graph demonstrating the effect of A2 scFv on the accumulation of calcein in MDR and Pgp-overexpressing $2780^{ADR}$ cells, in a fluorometer assay. The graph shows a positive dose-response effect of A2 scFv, administered prior to the addition of calcein, on the uptake of calcein by $2780^{ADR}$ cells. FIG. 3d is a plot demonstrating the effect of A2 scFv on calcein uptake by MDR and Pgp-overexpressing $2780^{ADR}$ cells. The A2 scFv was administered to cells prior to the addition of calcein. The plot shows a substantially higher (4-5 fold) mean of fluorescence intensity, indicating a substantial increase in calcein uptake by MDR cells treated with A2 scFv, as compared with cells not treated with A2 scFv. FIG. 3e is a bar graph illustrating specificity of scFv. The graph presenting data obtained by a fluorometer assay and shows that administration of A2 scFv to $2780^{ADR}$ cells, followed by to addition of calcein, substantially increased the cells' fluorescence intensity, indicating increased calcein uptake in cells. In comparison, the administration of a non-target scFv G1 (isolated against a melanoma tumor antigen) to the $2780^{ADR}$ cells, did not increase calcein uptake in cells.

FIG. 4a is a bar graph presenting data obtained by a fluorometer assay comparing calcein uptake in a rodent (CHO) MDR cell line $EMT^{R1}$. The graph shows that cells treated with A2 scFv, followed by addition of calcein, exhibited substantially higher levels of fluorescence, which is indicative of higher calcein uptake in cells, as compared with the untreated (negative) control. The effect of A2 scFv was similar to the effect of verapamil, a reference MDR modulator used as a positive control. FIG. 4b is a bar graph presenting data obtained by a fluorometer assay comparing calcein uptake in a MDR human epidermoid cell line KB-V1. The graph shows that cells treated with A2 scFv, followed by addition of calcein, exhibited substantially higher levels of fluorescence, which is indicative of higher calcein uptake in cells, as compared with the untreated (negative) control. The effect of A2 scFv was similar to the effect of verapamil, a reference MDR modulator used as a positive control. FIG. 4c is a bar graph presenting data obtained by a fluorometer assay comparing calcein uptake in a drug-sensitive 2780 cell line (the parental line of 2780$^{ADR}$). The graph showed similar fluorescence intensity observed in cells treated by A2 scFv, untreated (negative) control, or verapamil (positive) control, thus indicating no effect exerted by A2 scFv on calcein uptake in the drug-sensitive cells.

FIG. 5 is a plot presenting calcein uptake in 2780$^{ADR}$ cells treated with various concentrations of A2 scFv. The plot shows a dose-response curve of fluorescence intensity, indicative of calcein uptake. The estimated saturation (IC$_{100}$) and IC$_{50}$ concentrations are 0.1 and 0.065 mg A2 scFv per ml, respectively (or 4 and 2.6 μM, respectively).

FIG. 6 is a bar graph presenting the effect of A2 scFv on the viability of 2780$^{ADR}$ cells treated with various concentrations of doxorubicin. The viability of cells was determined by [$^3$H]-leucine incorporation into cellular proteins. The graph shows that treating cells with A2 scFv, prior to the addition of doxorubicin, resulted in substantial loss of viability of cells, as compared with cells not treated with A2 scFv.

DESCRIPTION OF THE PREFERRED EMBODIMENTS

Figure 4A:
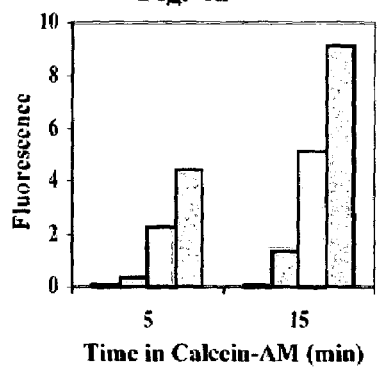
FIGS. 4a-c demonstrate the effect of A2 scFv on drug efflux activity in various MDR cell lines and their parental drug-sensitive cell lines.

The present invention is of an antibody fragment which includes an antigen binding-site capable of binding extracellular P-glycoprotein (Pgp), and as such, can be used for inhibiting drug efflux activity in multidrug resistant (MDR) cells, or in detecting MDR cells.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein the term "P-glycoprotein" refers to a 170 kDa trans-membrane protein encoded by the human mdr1 gene, which functions as an energy-depended biological pump in multidrug resistant cells.

As used herein the phrase "multidrug resistance" refers to the resistance of some cells, such as cancer cells overexpressing Pgp, to cytotoxic drugs.

As used herein the phrase "antibody fragment" refers to any active portion of a native antibody molecule. Examples of antibody fragments include, but are not limited to an Fv, a single chain Fv, a Fab, a F(ab')$_2$ or a Fab'. An antibody fragment may be produced enzymatically or chemically from an intact antibody, or may be synthetically produced. Alternatively, an antibody fragment may be expressed from a polynucleotide sequence encoding the antibody fragment sequence.

As used herein the term "Fv" refers to a polypeptide comprising one variable light chain (V$_L$) domain and one variable heavy chain (V$_H$) domain of an antibody molecule held together by noncovalent interactions. An Fv includes the antigen binding region of the antibody molecule.

As used herein the phrase "single chain Fv" (scFv) refers an Fv in which the V$_L$ and V$_H$ domains are connected preferably by a polypeptide linker. The scFv is the smallest antibody fragment that bears the complete antigen binding site.

As used herein the term "Fab" refers to the polypeptide comprising an antibody fragment which is essentially equivalent to that obtained by digestion of the antibody with the enzyme papain.

As used herein the term "F(ab')$_2$" refers to the polypeptide comprising an antibody fragment which is essentially equivalent to that obtained by digestion of the antibody with the enzyme pepsin at pH 4.0-4.5.

As used herein the term "Fab'" refers to the polypeptide comprising an antibody fragment which is essentially equivalent to that obtained by reduction of the disulfide bridge or bridges joining the two heavy chain pieces of a F(ab')$_2$.

Several Pgp-specific monoclonal antibodies (Mab) which are capable of binding Pgp and thereby circumventing drug-efflux activity in MDR cells have been described in the prior art [U.S. Pat. Nos. 4,837,306, 5,766,946 and 6,479,639; Meyers, M. B. et al., Cancer Res., 49:3209 (1987); O'Brien, J. P. et al., Proc. Amer. Assoc. Cancer Res., 30:Abs 2114 (1989); Cinciarelli, C., et al., Int. J. Cancer, 47:533 (1991) Hamada H., et al., Cancer Res. PNAS 83:7785 (1986); Pearson, J. W., et al., J. Natl. Cancer Inst. 88:1386 (1991); Tsuruo, T., et al., Jpn. J. Cancer Res. 80:627 (1989); Hamada H. et al., cancer Res. 50:3167 (1990)]. Yet, thus far, practical therapeutic use of such anti-Pgp Mabs has been hampered mainly by the large size of these molecules which limits the mobility and tissue penetration thereof [Yokota et al., Cancer Res. 52: 3402-3408 (1992)]. In addition to tissue penetration and mobility limitations, these large Mab molecules would be slow to clear out from body circulation, and thus as a consequence could potentially damage non-target tissue (12). Furthermore, these Mabs which typically display high affinity to Pgp may also be toxic to normal cells that physiologically express Pgp (27).

One way of circumventing of these limitations, is to use an antibody fragment. Advantageously, the antibody fragment would have a small molecular size, yet a high specificity and moderate affinity to Pgp and thus would be highly efficient in inhibiting drug efflux activity in MDR cells yet devoid of the abovementioned limitations.

The possible use of an antibody fragment to overcome deficiencies of a monoclonal antibody molecule (Mab), was illustrated by Schodin and Kranz [J. Biolog. Chem. 268: 25722-25727 (1993)]. It was found that while monoclonal antibodies effectively inhibited activation of T cells in vitro, they also caused substantial undesirable side effects when used in vivo. These side effects were effectively circumvented by replacing the Mab with a small size scFv.

U.S. Pat. No. 6,479,639 discloses a Pgp-specific Mab and the prospect of using portions thereof in therapy. It further describes enzymatic, chemical and genetic engineering techniques known in the art, which could be utilized for generating antibody fragments. Yet, the patent disclosure does not provide any examples of an actual Mab-derived fragment or specific methodology for generating same.

The fact that an antibody fragment capable of specifically binding Pgp and also capable of modulating cellular MDR activity is not described in this or any other prior art document indicates that generation of functional antibody fragments from existing Mab sequences is not trivial.

This indication is supported by a recent study conducted by Niv and co-workers (19). This study generated and characterized a Pgp-specific Mab, termed "9F11", and an scFv derived from this Mab. Both molecules, the complete 9F11 Mab as well as its scFv derivative, specifically targeted extracellular Pgp in MDR cells. However, while the 9F11 whole Mab was also capable of inhibiting drug-efflux activity in MDR cells, its scFv derivative was not (unpublished data).

Hence, the mere suggestion of U.S. Pat. No. 6,479,639 that Mab sequences can be utilized for generating a respective antibody fragment without actual demonstration that such an antibody fragment would be active in inhibiting drug-efflux activity in MDR cells does not provide an ordinary skilled artisan with motivation to generate such antibody fragment sequences since reasonable degree of success cannot be ensured.

The present invention provides a novel Pgp-specific antibody fragment which is capable of effectively inhibiting the drug-efflux activity in multidrug resistant cells.

Thus, according to one aspect of the present invention there is provided an antibody fragment which includes an antigen-binding region capable of binding an extracellular portion of P-glycoprotein (Pgp), and which is also capable of at least partially inhibiting the drug efflux activity in multidrug resistant cells.

Preferably, the antibody fragment is directed to the 170 kDa Pgp expressed by the human mdr1 gene. Although several regions of this protein can potentially be targeted, the antibody fragment of the present invention is preferably directed to an epitope located in the first extracellular loop of the 170 kDa polypeptide Pgp which is expressed by the human mdr1 gene. Most preferably, the antibody fragment is directed to the amino acid sequence of SEQ ID NO:1.

The antibody fragment of the present invention can be generated using phage display techniques such as described in the following references: U.S. Pat. Nos. 5,698,426; 5,658, 727; 5,223,409; 5,403,484; 5,580,717; 5,427,908; 5,750, 753; 5,821,047; 5,571,698; 5,427,908; 5,516,637; 5,780, 225; 5,658,727; 5,733,743 and 5,969,108; and PCT application No. PCT/GB91/01134; PCT publications WO 90/02809; WO 91/10737; WO 92/01047; WO 92/18619; WO 93/11236; WO 95/15982; WO 95/20401; and Hoogenboom et al. Immunotechnology 4:1-20 (1998); Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); and Burton et al., Advances in Immunology 57:191-280 (1994).

Accordingly, a target antigen may be utilized to immunize a host animal using immunization protocols well known in the art. Preferably, the target antigen is derived from P-glycoprotein (Pgp), more preferably the target antigen is derived from the 170 kDa Pgp expressed by the human mdr1 gene. Most preferably, the target antigen is derived from the first loop of the 170 kDa Pgp, and includes the amino acid sequence of SEQ ID NO:1.

Following immunization, the mRNA of B-cells can be extracted from spleen, peripheral blood lymphocytes, bone-marrow or tonsil of the immunized animal. The mRNA can then be utilized to construct an antibody fragment phage-display library, using methodology such as that described by Hoogenboom et al. [Immunotechnology 4:1-20 (1998)]; Kand et al. [Proc. Natl. Acad. Sci. 88:4363 (1991)]; Barbas et al. [Proc. Natl. Acad. Sci. 88:7978 (1991)], Garrard et al. [Biotechnology 9:1373-1377 (1991)]; Hoogenboom et al. [Nucleic Acids Res. 19:4133-4137 (1991)]; and Sharon et al. [Combinational Chemistry & High Throughput Screening 3:185-196 (2000)].

Recombinant phages possessing desirable antibody binding properties can be selected by sequential enrichment of specific-target binding phages from a large excess of non-binding clones. This selection can be achieved by a number of optional techniques including panning on immobilized antigen; panning using specific elution; using biotinylated antigen; affinity purification on columns; or direct panning on cells. Suitable selection techniques are described by, for example, Pluckthum [The Pharmacology of Monoclonal Antibodies, Vol 113: Rosenburg and Moors eds. Springer-Verlag, New York, pp. 269-315 (1994)] and Hoogenboom et al. [Immunotechnology 4: 1-20 (1998)].

Following selection, the phages bearing nonspecific antibody fragments may be removed by washing and the bound phages, bearing target-specific antibody fragments, are eluted and amplified by infection of E. coli. Once the recombinant phages, displaying the target-specific antibody fragment, have been isolated, the polynucleotide sequence encoding the antibody can be recovered from the phage display package and cloned into a recombinant expression vector using standard methods known in the art, such as described by Ausubel et al. eds. [Current Protocols in Molecular Cloning (1989), Greene Publishing and Wiley Interscience, New York, N.Y.].

An antibody fragment generated as described above can be characterized for Pgp specificity and affinity by any conventional immunoassay technique known in the art, including, but not limited to, the ELISA, radioimmunoassays, or immuofluorescence assays. The effect of an antibody fragment on inhibiting the drug-efflux activity in MDR cells, may be assessed by monitoring intracellular accumulation or efflux of the drug of interest, in the present or absence of an antibody fragment. For example, Cole et al. [Cancer Res. 54:5902-5910 (1994)] describe cellular accumulation and efflux assays which can be used for evaluating the efflux of drugs and/or toxins such as, but not limited to, doxorubicin, vincristine, colchicines, VP-16, vinblastine, verapamil, mitoxantrone, taxol, Cyclosporin A, quinidine, progesterone, tamoxifen, epirubicin, daunorubicin, and MX2. Additional suitable characterization assays include flow-cytometer or fluorometer assays which capitalize on the fluorescent properties of a drug, such as doxorubicin or daunorobicin [U.S. Pat. No. 5,556,856; Krishan Math. Cell Biol. 33:491-500 (1990)], or alternatively, based on fluorescent dyes such as rhodamine or calcein [U.S. Pat. No. 5,403,574; Hollo et al., Biochim. Biophys Acta 1191:384-388 (1994)]. The effect of an antibody fragment on increasing cytotoxicity to MDR cells may be assessed by monitoring cellular uptake of vital dyes following a period of exposure to a cytotoxin, such as the methods described in U.S. Pat. No. 5,543,423; or by assessment of incorporation of [$^3$H]Leucine, such as the method described in Example 3 of the example section that follows.

Example 1 of the Examples section which follows describes the isolation of an anti-Pgp single-chain antibody fragment (scFv).

Briefly, the amino acid sequence SEQ ID NO:1 was batch-cloned into a f88 filamentous phage in fusion to a gene encoding a coat protein. The recombinant display phage was then used to immunize mice in order to generate an immune response to the target antigen (SEQ ID NO:1) using standard methods known in the art. Following immunization, the spleen was removed from the immunized mice and the mRNA was extracted from splenic B cells. The isolated mRNA was then used to generate and amplify cDNA using standard RT-PCR techniques. Following RT-PCR the amplified sequences were used to generate a phage display library which was screened using the target antigen. Polynucleotide sequences encoding the scFv were isolated from positive phage clones using standard molecular techniques. The isolated polynucleotide sequence (SEQ ID NO:2) was cloned into a prokaryotic expression vector and expressed in E. coli. The expressed scFv was then purified from the periplasmic fraction of these cells, using standard purification methods (further description of scFv expression and purification is provided herein bellow).

As illustrated in Examples 2 and 3 of the Examples section which follows, the novel single-chain Fv generated according to the teachings of the present invention (termed "A2") is a relatively small molecule (about 30 kDa) which exhibits high specificity of binding to extracellular Pgp and multidrug resistant cells and a moderate binding affinity (about 150 nM) to Pgp. Furthermore this scFv is capable of effectively inhibiting drug efflux activity in MDR cells and as a result is capable of effectively increasing drug cytotoxicity in MDR cells.

As is mentioned hereinabove, a preferred approach for synthesizing the anti-Pgp scFv of the present invention is to isolate and express scFv encoding sequences.

As used herein the term "express" refers to the conversion of a polynucleotide sequence into a polypeptide.

Accordingly, the isolated polynucleotide sequence encoding the scFv polypeptide can be ligated to appropriate regulatory elements to generate a nucleic acid construct. Preferably, the nucleic acid construct is an expression construct (i.e., an expression vector) which includes a promoter selected suitable for directing transcription of the isolated nucleic acid sequence encoding the polypeptide of this invention in a particular host cell.

Any suitable promoter sequence can be used by the nucleic acid construct of the present invention. Preferably, the promoter utilized by the nucleic acid construct is active in the specific cell being transformed. The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells. The construct according to the present invention can be, for example, a plasmid, a bacmid, a phagemid, a cosmid, a phage, a virus or an artificial chromosome.

A variety of prokaryotic or eukaryotic cells can be used as host-expression systems to express the polypeptide coding sequence. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence. Mammalian expression systems can also be used to express the polypeptide of the present invention. Bacterial systems are preferably used to produce recombinant polypeptides since they enable a high production volume at low cost.

In bacterial systems, a number of expression vectors can be advantageously selected depending upon the use intended for the polypeptide expressed. For example, when large quantities of polypeptide are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the polypeptide may also be desirable. Such vectors adaptable to such manipulation include, but are not limited to, the pET series of E. coli expression vectors [Studier et al., Methods in Enzymol. 185:60-89 (1990)].

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the polypeptide coding sequence can be driven by a number of promoters. For example, viral promoters such as the 35S RNA and 19S RNA promoters of CaMV [Brisson et al. Nature 310:511-514 (1984)], or the coat protein promoter to TMV [Takamatsu et al. EMBO J. 6:307-311 (1987)] can be used. Alternatively, plant promoters can be used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other then containing the necessary elements for the transcription and translation of the inserted coding sequence (encoding the polypeptide), the expression construct of the present invention can also include sequences engineered to optimize stability, production, purification, yield or activity of the expressed polypeptide.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant polypeptides of the present invention may either remain within the recombinant cell, secreted into the fermentation medium, secreted into a space between two cellular membranes, such as the periplasmic space in E. coli; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in "substantially pure" form.

As used herein, the phrase "substantially pure" refers to a purity that allows for the effective use of the protein in the applications described herein.

In addition to being synthesizable in host cells, the polypeptide of the present invention can also be synthesized using in vitro expression systems. These methods are well known in the art and the components of the system are commercially available.

Further alternatively, the polypeptide of the present invention can also be synthesized using, for example, standard solid phase techniques. Such techniques include exclusive solid phase synthesis, partial solid phase synthesis methods, fragment condensation, classical solution synthesis, and even by recombinant DNA technology, such as described by Merrifield, J. [Am. Chem. Soc., 85:2149 (1963)]. Solid phase polypeptide synthesis procedures are well known in the art and further described by John Morrow Stewart and Janis Dillaha Young [Solid Phase Peptide Syntheses, 2nd Ed., Pierce Chemical Company, (1984)].

The synthetic polypeptide can be purified by preparative high performance liquid chromatography procedure, such as described by Creighton T. [Proteins, structures and molecular principles, W. H. Freeman and Co. N.Y. (1983)] and the composition of which can be confirmed via amino acid sequencing.

Since the antibody fragment of the present invention is Pgp-specific it can be used to detect multidrug resistant (MDR) cells. A key mechanism of MDR is the overexpression of Pgp and a clear correlation was established between overexpression of Pgp and the lack of response to chemotherapy of cancer patients (6,7). Thus, if chemotherapy is applied non-effectively, considerable damage may result from non target toxicity coupled with missed opportunity to provide another, more effective treatment. Hence, an accurate, specific and reliable diagnosis of MDR cells in cancer patients would be a most useful clinical tool to determine options and selecting the most appropriate treatment to administer.

Thus, according to another aspect of the present invention there is provided a method for detecting multidrug resistant cells. The method includes exposing cells to the antibody fragment of this invention, followed by detecting the antibody fragment bound to cells overexpressing Pgp, thereby detecting multidrug resistant cells. Preferably, the antibody fragment is labeled with a detectable moiety (described below) and which can be detected using standard immunoassays known in the art, such as ELISA, immunofluorescence, radioimmunoassay and immunohistochemical staining.

Initially, a biological sample, containing cells suspected of being MDR cells, such as tumor cells, is obtained from the individual for ex vivo analysis. In order to prevent sampled cells from being degraded, the cells can be stored at temperature below −20° C. until analyzed. Upon analysis, the cells are exposed to the antibody fragment and the antibody-cell binding is determined using any of the conventional in vitro immunoassay techniques known in the art. For example, a tumor section can be exposed to the antibody fragment of this invention on a microscope slide and analyzed using standard immunohistochemical techniques.

Cells of an individual suspected of having multidrug resistant cells, such as a cancer patient, can also be exposed to the antibody fragment in vivo. In such cases, the antibody fragment is labeled with a detectable moiety, such as radioactive moiety, e.g., $^3$H, $^{35}$S, $^{14}$C, $^{32}$P or $^{125}$I using standard techniques and the labeled antibody fragment is administered to an individual suspected of having cells overexpressing Pgp, preferably parenterally. Following a predetermined time period, changes in radioactivity levels in host cells are assessed using scintillation counting, auto-radiography or imaging techniques.

The methodology described hereinabove is preferably practiced using a detection kit. The kit includes the antibody fragment of the present invention, which is preferably labeled with a detectable moiety such as a chromogenic moiety (e.g., biotin), a fluorogenic moiety (e.g., fluorescein), a light-emitting moiety (e.g., luminol) or a radioactive moiety (e.g., $^{125}$I). The kit also includes reagents suitable for detecting the detectable moiety packaged in a container and identified in print on or in the package for use in diagnosing multidrug resistant cells. Procedures for labeling antibodies with such detectable moieties are described in, for example, "Using Antibodies: A Laboratory Manual" [Ed Harlow, David Lane eds., Cold Spring Harbor Laboratory Press (1999)] and the detection of such labeled antibodies can be accomplished using standard immunoassay procedures well known in the art.

As illustrated in the Examples section which follows, the anti-Pgp antibody fragment of this invention is highly suitable for use as an inhibitor of the drug efflux activity in multidrug resistant (MDR) cells, particularly for the following attributes: (i) it has a relatively small molecular size thereby conferring improved mobility and delivery to target cells, as well as short circulation in body fluids which minimizes undesired interactions with non-target cells; (ii) it has moderate affinity to Pgp which further minimizes interactions with non-target cells; and (iii) it is capable of being expressed ex vivo and in vivo.

Accordingly, the antibody fragment of this invention can be effectively used to substantially improve chemotherapy of individuals having multidrug resistant cancer cells.

Thus, according to another aspect of the present invention there is provided a method of treating cancer in an individual which includes providing the antibody fragment of this invention to an individual having cancer, and administrating the individual a therapeutically effective amount of an anti cancer agent, preferably an agent which is cytotoxic to cancer cells. The anti cancer drug may be administered prior to, concomitantly with, or following providing the antibody fragment. Preferably, the antibody fragment is provided to the patient sufficiently in advance of administering the anti cancer agent so as to allow the antibody fragment to penetrate to the individual's tumors containing MDR cells, to bind MDR cells, and to impair the drug-efflux capacity of such cells. The time interval required can be determined by routine pharmacokinetic methods and should be expected to vary with age, weight, and body size of the individual, as well as the location and condition of tumors containing the target MDR cells.

The phrase "anti cancer agent" and the phrase "chemotherapeutic drug" are used interchangeably herein and refer to a drug which can be used to treat cancer.

As used herein the term "treat" refers to substantially inhibiting, slowing or reversing the progression of a disease, such as cancer.

The antibody fragment may be provided by directly administrating the antibody fragment to the individual, or alternatively, by expressing the antibody fragment within cells of the individual.

When directly administrated, the antibody fragment is preferably introduced parenterally. It can be administered intravenously, intraperitoneally, retroperitoneally, intracistemically, intramuscularily, subcutaneously, topically, intraorbitally, intranasally or by inhalation. One or several doses may be administered as appropriate to achieve a sufficient level of antibody fragment bound to target MDR cells so as to produce an effective inhibition of drug efflux activity in the MDR cells to be eradicated by chemotherapy. The overall dosage and administration protocol for treatment with the antibody fragment and an anti cancer agent, may be designed and optimized by the clinical physician through the application of routine clinical skill.

The antibody fragment of this invention can also be provided by being expressed in cells of the individual. Preferably, the antibody fragment being expressed is a single-chain Fv (scFv). Further preferably, the antibody fragment is being expressed selectively in target cells such as, but not limited to MDR cancer cells, or in cells surrounding MDR cancer cells (e.g., non MDR tumor cells), or in hematopoietic cells reaching MDR cancer cells. Expression of the antibody fragment in human cells can be effected by introducing the polynucleotide sequence of this invention into the target cells in a manner enabling transient or stable transformation and expression.

Introduction of the polynucleotide sequence of this invention into target cells may be accomplished either ex vivo or in vivo. In the ex vivo approach, cells are removed from an individual and transformed with the polynucleotide sequence of this invention while being cultured. The transformed cells are further expanded in culture and then returned to the individual. The ex-vivo approach is highly suitable for use along with autologous bone-marrow transplants. In such procedures, bone marrow cells are removed from the body of a cancer patient, hematopoietic stem cells are enriched, the patient treated with extensive chemotherapy, and finally, the cultured stem cells are replanted into the patient in order to enable hematopoietic cell regeneration.

In such procedures, chemotherapy often fails to eradicate all cancer cells due to survival of multidrug resistance (MDR) cells. The recurrence of cancer following such extensive chemotherapy, when the body is drastically immuno-compromised, is most devastating. Use of the method of the present invention along with autologous bone marrow transplant can inhibit MDR activity and substantially decrease the likelihood of cancer recurrence.

The antibody fragment coding sequences can be introduced into the hematopoietic stem cells removed from the body and subsequently expressed and secreted from these cells in vivo thereby targeting MDR cancer cells and substantially improving the efficacy of chemotherapy.

In the in vivo approach, the polynucleotide is introduced directly to target cells within the individual. The polynucleotide of this invention can be introduced into cells by any one of a variety of known methods within the art. Such methods can be found generally described in Sambrook et al., [Molecular Cloning: A Laboratory Manual, Cold Springs Harbor Laboratory, New York (1989, 1992)]; Ausubel et al., [Current Protocols in Molecular Biology, John Wiley and Sons, Baltimore, Md. (1989)]; Chang et al., [Somatic Gene Therapy, CRC Press, Ann Arbor, Mich. (1995)]; Vega et al., [Gene Targeting, CRC Press, Ann Arbor Mich. (1995)]; Vectors [A Survey of Molecular Cloning Vectors and Their Uses, Butterworths, Boston Mass. (1988)] and Gilboa et al. [Biotechniques 4 (6): 504-512 (1986)] and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods for inducing homologous recombination.

A preferred approach for introducing a polynucleotide encoding the antibody fragment of the present invention into cells of an individual, is by using a viral vector. Viral vectors offer several advantages including higher efficiency of transformation, and targeting to, and propagation in, specific cell types. Viral vectors can also be modified with specific receptors or ligands to alter target specificity through specific cell receptors, such as cancer cell receptors.

Retroviral vectors represent one class of vectors suitable for use with the present invention. Defective retroviruses are routinely used in transfer of genes into mammalian cells (for review see Miller, A. D., Blood 76: 271 (1990)]. A recombinant retrovirus including a polynucleotide encoding the antibody fragment of the present invention can be constructed using well known molecular techniques. Portions of the retroviral genome can be removed to render the retrovirus replication defective and the replication defective retrovirus can then packaged into virions, which can be used to infect target cells through the use of a helper virus and while employing standard techniques. Protocols for producing recombinant retroviruses and for infecting cells in vitro or in vivo with such viruses can be found in, for example, Ausubul et al., [eds, Current Protocols in Molecular Biology, Greene Publishing Associates, (1989)]. Retroviruses have been used to introduce a variety of genes into many different cell types, including epithelial cells endothelial cells, lymphocytes, myoblasts, hepatocytes and bone marrow cells.

Another suitable expression vector may be an adenovirus vector. The adenovirus is an extensively studied and routinely used gene transfer vector. Key advantages of an adenovirus vector include relatively high transduction efficiency of dividing and quiescent cells, natural tropism to a wide range of epithelial tissues and easy production of high titers [Russel, W. C. [J. Gen. Virol. 81: 57-63 (2000)]. The adenovirus DNA is transported to the nucleus, but does not integrate thereinto. Thus the risk of mutagenesis with adeno viral vectors is minimized, while short term expression is particularly suitable for treating cancer cells, such as multidrug resistant cancer cells. Adenoviral vectors used in experimental cancer treatments are described by Seth et al. [Adenoviral vectors for cancer gene therapy. In: P. Seth (ed.) Adenoviruses: Basic biology to Gene Therapy, Landes, Austin, Tex., (1999) pp. 103-120].

A suitable viral expression vector may also be a chimeric adenovirus/retrovirus vector which combines retroviral and adenoviral components. Preliminary results using such vectors to transduce tumor cells suggest that this new type of viral expression vector is more efficient than traditional expression vectors [Pan et al., Cancer Letters 184: 179-188 (2002)].

A specific example of a suitable viral vector for introducing and expressing the polynucleotide sequence of this invention in an individual is the adenovirus-derived vector Ad-TK. This vector expresses a herpes virus thymidine kinase (TK) gene for either positive or negative selection and includes an expression cassette for desired recombinant sequences. This vector can be used to infect cells that have an adenovirus receptor which includes most cancers of epithelial origin [Sandmair et al. [Hum. Gene. Ther. 11: 2197-2205 (2000)].

Features that limit expression to particular cell types can also be included. Such features include, for example, promoter and regulatory elements that are specific for the desired cell type. The viral vector may also include a nucleotide sequence encoding a signal for secretion of the antibody fragment to the outside of the cell. Secretion signals generally contain a short sequence (7-20 residues) of hydrophobic amino acids. Secretion signals suitable for use in this invention are widely available and are well known in the art, see, for example by von Heijne [J. Mol. Biol. 184:99-105 (1985)] and by Lej et al., [J. Bacteriol. 169: 4379 (1987)].

The recombinant vector can be administered in several ways. If viral vectors are used the procedure can take advantage of their target specificity and consequently, such vectors do not have to be administered locally at the tumor site. However, local administration can provide a quicker and more effective treatment. Administration of viral vectors can also be performed by, for example, intravenous or subcutaneous injection into the subject. Following injection, the viral vectors will circulate until they recognize host cells with appropriate target specificity for infection.

The antibody fragment of the present invention, or the polynucleotide encoding same, can be provided to an individual per se or as an active ingredient of a pharmaceutical composition which also includes a suitable carrier.

The pharmaceutical composition of the present invention can further include a chemotherapeutic drug, preferably a chemotherapeutic drug which is toxic to cancer cells such as, but not limited to, doxorubicin, vincristine, colchicines, VP-16, vinblastine, verapamil, mitoxantrone, taxol, Cyclosporin A, quinidine, progesterone, tamoxifen, epirubicin, daunorubicin, and MX2.

The pharmaceutical composition may be administered in either one or more of ways depending on whether local or systemic treatment is of choice, and on the area to be treated. Administration may be done topically (including ophtalmically, vaginally, rectally, intranasally), orally, by inhalation, or parenterally, for example by intravenous drip or intraperitoneal, subcutaneous, intramuscular or intravenous injection. Preferably, the pharmaceutical composition is administered parenterally.

Pharmaceutical compositions for parenteral administration include aqueous solutions of the active preparation in water-soluble form. Additionally, suspensions of the antibody fragment may be prepared as appropriate oily injection suspensions. Suitable lipophilic solvents or vehicles include fatty oils such as seasame oil, or synthetic fatty acids esters such as ethyl oleate, triglycerides or liposomes. Aqueous injection suspensions may contain substances, which icrease the viscosity of the suspension, such as sodium carboxylmethyl cellulose, sorbitol or dextran. Optionally, the suspension may also contain suitable stabilizers or agents which increase the solubility of the antibody fragment to allow for the preparation of highly concentrated solutions.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Isolation of A2 Single-Chain Fv

Generation of Peptide Display Constructs for Immunization:

The peptide sequence GEMTDIFANAGNL (SEQ ID NO:1) which corresponds to amino acids 73-85 of the first putative extracellular loop of human P-glycoprotein (Pgp, GenBank Accession number NM 000927.2) was synthesized as described by Niv et al (19). Recombinant phages that display this amino acid sequence were generated using the HinDIII and PstI cloning sites of the filamentous bacteriophage f88, as described by Frenkel and Solomon (17). The recombinant filamentous bacteriophage f88 were used to immunize mice in three intraperitoneally injection, of $10^{11}$ phage units in PBS per injection, at 14 days intervals. Serum samples collected from the immunized mice were examined by ELISA for immunoreactivity with this peptide. The mice exhibiting a specific immune response to the target peptide were selected to construct a single-chain Fv (scFv) phage-display library.

Construction and Screening of scFv Library:

A scFv phage display library was generated using RNA extracted from spleen cells of the phage immunized mice described above, according to the procedure described by Clackson et al. [(Nature 352:624-628 (1991)]. Briefly, polynucleotide segments corresponding to the immunoglobulin heavy (VH) and light (VL) chain variable domains, were amplified from the mRNA spleen B-cells of immunized mice by RT-PCR, using specific sets of degenerate primers. The VH and VL PCR pools were assembled into a single-chain Fv repertoire by a PCR overlap extension reaction and subsequently cloned as an SfiI-NotI fragment into the pCANTAB6 phagemid vector. The complexity of the library was $1\times10^7$ independent clones. For panning, the library was first depleted from streptavidin binders by incubation with streptavidin-coated magnetic beads. A biotinylated peptide comprising the amino acid sequence of SEQ ID NO:1 (1 µM) was then incubated with $10^{11}$ cfu of the depleted library (1 hr, at room temperature) followed by addition of streptavidin-coated magnetic beads. Bound phages were eluted by using 1 ml of triethylamine (100 mM, pH 12) for 5 min at room temperature, followed by neutralization with 0.1 ml of 1 M Tris-HCl, pH 7.4. Eluted phages were expanded in exponentially growing E. coli TG1 cells that were later superinfected with M13KO7 helper phage as described by Hoogenboom et al (16).

As illustrated in Table 1 below, a progressive and marked enrichment, of phages that bind the peptide of SEQ ID NO:1, was observed after 3 rounds of panning. Twenty phage clones out of 84 analyzed following the 3$^{rd}$ round of panning exhibited binding activity toward the peptide (data not shown). Fingerprint analysis by means of multicutter restriction enzyme digestion of 10 peptide-specific clones revealed that they had a similar digestion pattern, suggesting that all were similar or identical (data not shown). DNA sequencing of VH and VL domains from these clones revealed that all were identical, suggesting that they were all derived from a single productive antibody during the VH/VL combinatorial event. Sequence analysis and comparison to the Kabbat database revealed that the A2 VH domain belongs to subgroup II of mouse heavy chain and the VL domain to the mouse Kappa II subgroup of light chains. The nucleic acid sequence of the scFv constructed from these VH and VL domains is provided in SEQ ID NO:2.

TABLE 1

Selection of scFv phage library for binding the peptide of SEQ ID NO: 1

| Cycle | Input* | Output* | Ratio (O/I) | Enrichment |
|---|---|---|---|---|
| 1 | $1 \times 10^{10}$ | $1 \times 10^5$ | $1 \times 10^{-5}$ | 1 |
| 2 | $1 \times 10^{11}$ | $1 \times 10^7$ | $1 \times 10^{-4}$ | 300 |
| 3 | $1 \times 10^{11}$ | $2 \times 10^8$ | $2 \times 10^{-3}$ | 2,000 |

*Phage input and output was determined by titration, determining phage cfu of infected E. coli TG1 cells before and after each round of selection.

Expression and Purification of Soluble Recombinant scFv:

The A2 scFv sequence (SEQ ID NO:2) was rescued from the phage clone by PCR and was subcloned into the phagemid vector pCANTAB6, using the SfiI-NotI cloning sites. A Myc (SEQ ID NO:3) and hexahistidine tags were fused to the C-terminus of the scFv gene. The scFv antibody was expressed in BL21 (λDE3) cells and purified from the periplasmic fraction by metal-ion affinity chromatography, using the hexahistidine tag fused to the C-terminus. An SDS-PAGE analysis of the purified A2 scFv is presented in FIG. 1a.

Example 2

Specificity and Binding Properties of A2 scFv

The molecular profile of the A2 scFv antibody was analyzed by size-exclusion chromatography and revealed a single protein peak in a monomeric form with an expected molecular mass of approximately 30 kDa (data not shown). The yield of the A2 scFv was about 2% (2 mg of a highly pure protein in 1 liter culture).

The binding specificity of the purified A2 scFv antibody was determined via ELISA. A biotinylated target peptide having the amino acid sequence of SEQ ID NO:1, or a non-target MRP1 control peptide (provided at 10 µg in 100 µl) were each immobilized onto a flexible microtiter plate using BSA-biotin-streptavidin. A purified A2 scFv was then added, at different concentrations, to the peptide-coated plate and was detected with an anti Myc tag-HRP conjugate antibody.

The ELISA results, presented in FIG. 1b, show that A2 scFv antibody reacted positively and in a dose-dependent manner with the target Pgp-derived peptide (SEQ ID NO:1). By comparison, A2 scFv did not react with the non-target MRP1 control peptide.

The binding properties of A2 scFv were further characterized using a saturation ELISA. In this experiment, a biotinylated Pgp-derived peptide (SEQ ID NO:1) was bound to plates precoated with BSA-biotin and exposed to increasing amounts of A2 scFv. The ELISA results which are illustrated in FIG. 1c, show that A2 scFv binding to the target peptide was dose-dependent and saturable. By interpolating the amount of A2 scFv necessary for 50% of maximal binding the affinity constant was estimated at 150 nM, indicating moderate affinity.

In a competition binding radio-immunoassay the purified A2 scFv (100 µg) was first labeled with [$^{125}$I] using the Bolton-Hunter reagent. The [$^{125}$I]-labeled A2 scFv antibody was added as a tracer (3-5×10$^5$ cpm/well) to a flexible microtiter plate, which had been pre-coated with BSA-biotin and the target peptide (SEQ ID NO:1), as described above. A non-labeled (i.e., cold) A2 scFv was then added, as a competitor, to the pre-coated plates at increasing concentrations. Plates were incubated for 1 hr at room temperature, then washed and analyzed by gamma counter. The radio-immunoassay results, illustrated in FIG. 1d, show that the [$^{125}$I]-labeled A2 scFv antibody binding to the target Pgp-derived peptide (having the amino acid sequence SEQ ID NO:1) was dose-dependent. By interpolating the amount of the competitor (cold) A2 scFv necessary for 50% of maximal binding, the affinity constant was estimated at 130 nM, indicating a moderate affinity.

In another series of experiments, the reactivity and specificity of A2 scFv to Pgp, expressed on the surface of MDR cells, was evaluated. These experiments utilized human carcinoma cell lines that display a stable Pgp-dependent MDR phenotype, as well as their respective parental drug-sensitive cells. The MDR cell lines and the drug-sensitive cell lines used in these experiments are described in Table 2 below.

TABLE 2

| Tissue of Origin | MDR Cell Line | Drug-Sensitive Cell Line |
|---|---|---|
| Human ovarian carcinoma | 2780$^{ADR}$* | 2780* |
| Human epidermoid carcinoma | KBV-1** | KB3-1** |

*2780$^{ADR}$ was established from the drug sensitive 2780 cell line (21).
**KBV-1 was established from the drug sensitive KB3-1 cell line (24).

Drug sensitive cells and MDR cells ($5\times10^5$) were washed with PBS, and resuspended in RPMI-1640 medium (GIBCO). Cells growing on six well tissue culture plates were washed twice followed by incubation with soluble purified A2 scFv (50 μg/ml) for 90 minutes on ice. Detection was with anti-Myc (30 μg/ml) and FITC-labeled anti-mouse IgG (1:1000, Jackson). Detection of fluorescent cells was performed on a FACScalibur (Becton Dickinson).

FIGS. 2a-d demonstrate a comparative immuno-fluorescence flow-cytometer analyses, illustrating a strong reactivity of A2 scFv with the MDR cell lines 2780$^{ADR}$ (FIG. 2b) and KBV-1, while no reactivity was observed with the drug-sensitive cell lines 2780 (FIG. 2a) and KB3-1 (FIG. 2c).

The specificity and reactivity of the A2 scFv antibody to MDR and Pgp-overexpressing cells was further demonstrated by comparative immuno-histochemistry analysis. Drug sensitive cells and MDR cells were grown to 50% confluence on glass slides, pre-coated with 4% gelatin in PBS, fixed with 2% formaldehyde in PBS, blocked with 1% BSA in PBS at room temperature, then followed by 90 min incubation with A2 scFv (0.2 mg/ml) in PBS containing 1% BSA (room temperature). The slides were then covered with HRP-labeled anti-Myc-antibody (1:500, in PBS containing 1% BSA) for 1 hr, washes with water, then covered with peroxidase substrate, (AEC) for 2-3 min. Slides were then washed with water and counter staining was performed with hematoxylin. As illustrated in FIGS. 2e-h, the A2 scFv antibody displayed an intense in situ staining of MDR 2780$^{ADR}$ and KBV-1 cells (FIGS. 2e and 2g, respectively), while on the other hand, A2 scFv did not stain the respective drug-sensitive parental 2780 and KB3-1 cells (FIGS. 2f and 2h, respectively).

Hence, the results described hereinabove clearly demonstrate that the A2 scFv antibody selectively binds human cell surface-expressed Pgp and does not bind human drug-sensitive cells which lack, or marginally express Pgp.

Example 3

Biological Function of A2 scFv

The effect of A2 scFv on the drug-efflux activity of Pgp was evaluated in a series of chromophore efflux assays. The assays utilized the fluorescent Pgp hydrophobic-substrate calcein-AM (Molecular Probes, Eugene, Oreg.), as inverse relationship exist between the level of Pgp activity and the accumulation of calcein in MDR cells [Hollo et al (20)]. The A2 scFv was applied to human and rodent (CHO) cell lines that display a stable Pgp-dependent MDR phenotype, and their respective parental drug-sensitive cells, as described in the Table 3 below.

TABLE 3

| Tissue of Origin | MDR Cell Line | Drug-Sensitive Cell Line |
|---|---|---|
| Human ovarian carcinoma | 2780$^{ADR}$* | 2780* |
| Human epidermoid carcinoma | KBV-1** | KB3-1** |
| rodent (CHO) | EMT$^{R1}$*** | A8*** |

*2780$^{ADR}$ was established from the drug sensitive 2780 cell line (21).
**KBV-1 was established from the drug sensitive KB3-1 cell line (24).
***EMT$^{R1}$ was established from the drug sensitive A8 cell line (23).

Drug sensitive cells and MDR cells ($5\times10^5$) were washed with PBS, and resuspended in HPMI buffer (10 mM Hepes at pH 7.4 containing 120 mM NaCl, 5 mM KCl, 0.4 mM CaCl$_2$, 10 mM NaHCO$_3$, 0.5 mM Na$_2$HPO$_4$, and 10 mM glucose). The cell suspensions were pre-incubated for various times with various concentrations of the A2 scFv, then supplemented with 1 μM calcein-AM (a fluorescent Pgp hydrophobic substrate; Molecular Probes, Eugene, Oreg.) and allowed for 5-15 min incubation at 37° C. Following incubation, the treated and untreated cells were exposed to calcein and analyzed for fluorescence intensity (493-515 nm) by a standard fluorometer or by a flow cytometer (FACScalibur, Becton Dickinson).

FIG. 3a illustrate that the MDR cell line 2780$^{ADR}$, accumulated 5 and 10-fold less calcein (after 5 or 15 min incubation, respectively), as compared with the parental drug-sensitive 2780 cell line. Similarly, the results of a flow cytometer assay, illustrated in FIG. 3b, show that the MDR cell line 2780$^{ADR}$ exhibited substantially lower mean fluorescence intensity than the respective parental drug-sensitive 2780 cell line. These results clearly demonstrate the functional capacity of MDR and Pgp-overexpressed cells to extrude chromophoric substrates like calcein-AM.

In a similar experiment, A2 scFv was added to 2780$^{ADR}$ cells, for 10-30 minutes prior to the addition of calcein-AM. The A2 scFv treatment resulted in a substantial increase in fluorescence intensity of cells, indicating a substantial decrease in drug-efflux activity. Accordingly, FIG. 3c shows that the accumulation of calcein in cells treated with A2 scFv, was 4-5 fold higher than the accumulation of calcein in cells not treated with A2 scFv. The results illustrated in FIG. 3c further show that the inhibitory effect of A2 scFv on the drug-efflux activity of 2780$^{ADR}$ cells, was dose-dependent and exhibited maximal inhibitory activity at 100 μg/ml (i.e. 4 μM). The drug-efflux inhibitory effect of A2 scFv was similar to the drug-efflux inhibitory effect observed with 15 μM verapamil, a known modulator of Pgp drug efflux (8). A similar effect was observed via a flow cytometer analysis, as illustrated in FIG. 3d. These results indicate that the A2 scFv antibody can effectively inhibit the drug-efflux activity of human MDR and Pgp-overexpressing cells.

In another assay, the drug efflux modulating-activity of A2 scFv was compared with G1 scFv [isolated against a melanoma associated tumor antigen (22)]. The assay results, illustrated in FIG. 3e, show that while the A2 scFv substantially inhibited drug efflux activity of 2780$^{ADR}$, the G1 scFv antibody treatment had no effect.

The effect of A2 scFv on the drug efflux activity of other MDR and Pgp-overexpressing cell lines, and their parental drug-sensitive cell lines, was evaluated in a series of assays.

Figure 4B:
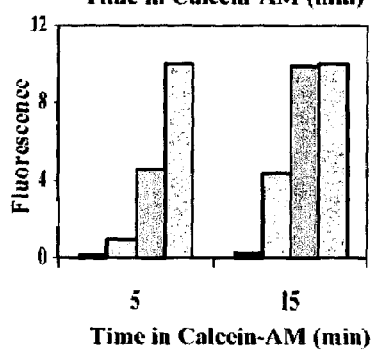
Figure 4C:
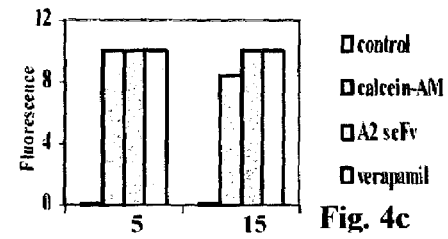
Figure 4D:
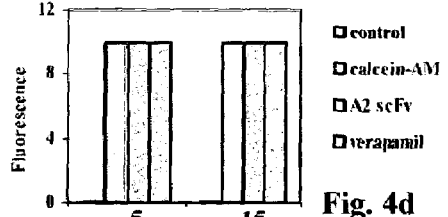
FIG. 4d is a bar graph presenting data obtained by a fluorometer assay comparing calcein uptake in a drug-sensitive human epidermoid cell line KB3-1 (the parental line of KBV-1). The graph shows similar fluorescence intensity observed in cells treated by A2 scFv, untreated (negative) control, or verapamil (positive) control, thus indicating no effect exerted by A2 scFv on calcein uptake in the drug-sensitive cells.
Figure 4E:
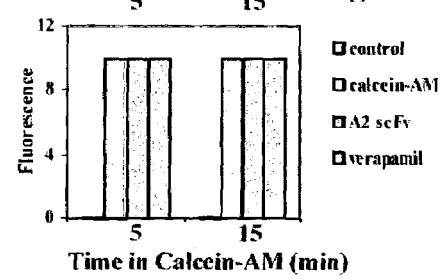
FIG. 4e is a bar graph presenting data obtained by a fluorometer assay comparing calcein uptake in a drug-sensitive rodent (CHO) cell line A8 (the parental line of EMT$^{R1}$). The graph shows similar fluorescence intensity observed in cells treated by A2 scFv, untreated (negative) control, or verapamil (positive) control, thus indicating no effect exerted by A2 scFv on calcein uptake in the drug-sensitive cells.

FIGS. 4a-b illustrate the effect of A2 scFv on the drug efflux activity of MDR and Pgp-overexpressing EMT$^{R1}$ and KBV-1 cells. The results show substantial increases in calcein accumulation, indicating drug-efflux inhibition in cells treated with A2 scFv To ascertain that the inhibitory activity of the A2 scFv molecule is not due to nonspecific cell toxicity, additional experiments were performed whereby A2 scFv was pre-incubated, prior to addition of calcein, with the drug sensitive cell lines 2780, KB3-1 and A8. The results, illustrated in FIGS. 4c-e, show that A2 scFv treatment did not affect the level of calcein accumulation in any of these cells, indicating no effect on the drug-efflux activity of drug-sensitive cells treated with A2 scFv.

The drug-efflux inhibition efficiency of A2 scFv was further evaluated in another assay in which the A2 scFv was provided, at increasing concentrations, to MDR 2780$^{ADR}$ cells, followed by the addition of calcein-AM. The results, illustrated in FIG. 5a, show that A2 scFv increased the accumulation of calcein in cells in a dose-dependant and saturable fashion. The minimal detectable inhibitory activity was observed with an A2 scFv concentration of 0.025 mg/ml (1 μM). The saturation inhibitory activity was observed with an A2 scFv concentration exceeding 0.1 mg/ml (4 μM). The concentration of A2 scFv molecule that inhibits 50% drug-efflux activity ($IC_{50}$) was estimated at 65 μg/ml (2.6 μM).

The effect of the A2 scFv molecule on the survival of 2780$^{ADR}$, exposed to doxorubicin (a chemotherapeutic drug), was evaluated based on the level of [$^3$H]Leucine in cells, an indicator of cell viability. Cells were pre-incubated with A2 scFv at a concentration of 0.2 mg/ml, then exposed to 5-10 μM of doxirubicin and then analyzed for [$^3$H] Leucine content. As illustrated in FIG. 5b, the A2 scFv treatment effectively reduced the viability of cells exposed to doxirubicin, as compared with cells not treated with A2 scFv. These results show that A2 scFv can inhibit the Pgp-mediated drug efflux activity in multi-drug resistant cells, thereby circumventing drug resistance.

Thus, in conclusion, the results presented herein clearly demonstrate that the A2 scFv antibody of the present invention selectively reacts with Pgp-overexpressing cells and is therefore an effective inhibitor of drug-efflux activity in multi-drug resistant cells.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Gottesman, M. M., and Pastan, I. Biochemistry of multidrug resistance mediated by the multidrug transporter. *Annu. Rev. Biochem.* 6:385-427, 1993.
2. Tan B, Piwnica-Worms D, Ratner L. Multidrug resistance transporters and modulation. *Curr Opin Oncol.* 12:450-8, 2000.
3. Sarkadi, B., and Muller, M. Search for specific inhibitors of multidrug resistance in cancer. *Semin. Cancer Biol.* 8: 171-82, 1997.
4. Riordan, J. R., and Ling, V. Purification of P-glycoprotein from plasma membrane vesicles of Chinese hamster ovary mutants with reduced colchicines permeability. *J. Biol. Chem.* 254:12701-12705, 1979.
5. Borst P, Elferink R O. Mammalian abc transporters in health and disease. *Annu Rev Biochem.* 71:537-92, 2002.
6. Roninson, I., Abelson, H. T., Housman, D. E., Howell, N., and Varshavsky, A. Amplification of specific DNA sequences correlates with multi-drug resistance in Chinese hamster cells. *Nature* 309:626-628, 1985.
7. Goldstein, L. J., Galski, H., Fojo, A., Willingham, M. C., Lai, S.-L., Gazadar, A., Pirker, R., Green, A., Crist, W., Brodeur, G. M., Lieber, M., Cossman, J., Gottesman, M. M., and Pastan, I. Expression of a multidrug resistance gene in human cancers. *J. Natl. Cancer Inst.* 81:116-124, 1989.
8. Tsuruo T, Iida H, Tsukagoshi S, Sakurai Y. Overcoming of vincristine resistance in P388 leukemia in vivo and in vitro through enhanced cytotoxicity of vincristine and vinblastine by verapamil. *Cancer Res.* 41:1967-72, 1981.
9. Hamada H, and Tsuruo T. Functional role for the 170- to 180-kDa glycoprotein specific to drug-resistant tumor cells as revealed by monoclonal antibodies. *Proc Natl Acad Sci USA* 83:7785-9, 1986.
10. Mechetner E B, and Roninson I B. Efficient inhibition of P-glycoprotein-mediated multidrug resistance with a monoclonal antibody. *Proc Natl Acad Sci USA* 89:5824-8, 1992.
11. Naito M, Tsuruo T. Monoclonal antibodies to P-glycoprotein: preparation and applications to basic and clinical research. *Methods Enzymol.;*292:258-65, 1998.
12. Jain R K Delivery of molecular medicine to solid tumors. *Science* 271:1079-1080, 1996.
13. Huston J S, Levinson D, Mudgett-Hunter M, Tai M S, Novotny J, Margolies M N, Ridge R J, Bruccoleri R E, Haber E, Crea R, Protein engineering of antibody binding sites: recovery of specific activity in an anti-digoxin single-chain Fv analogue produced in *Escherichia coli*. *Proc Natl Acad Sci USA* 85:5879-83, 1996
14. Bird R E, Hardman K D, Jacobson J W, Johnson S, Kaufman B M, Lee S M, Lee T, Pope S H, Riordan G S, Whitlow M. Single-chain antigen-binding proteins. *Science* 242:423-6, 1988.
15. Raag R, Whitlow M. Single-chain Fvs. *FASEB J* 9:73-80, 1995
16. Hoogenboom H R, de Bruine A P, Hufton S E, Hoet R M, Arends J W, Roovers R C. Antibody phage display technology and its applications. *Immunotechnology* 4:1-20, 1998.
17. Frenkel D, Solomon B. Filamentous phage as vector-mediated antibody delivery to the brain. *Proc Natl Acad Sci USA.* 99:5675-9, 2002.
18. Lev, A., Denkberg, G., Cohen, C J., Tzukerman, M., Skorecki, K L., Chames, P., Hoogenboom, H., and Reiter, Y. Isolation and characterization of human recombinant antibodies endowed with the antigen-specific, major histocompatibility complex-restricted specificity of T cells directed toward the widely expressed tumor T-cell epitopes of the telomerase catalytic subunit. *Cancer Res.* 62: 3184-3194, 2002.
19. Niv, R., Pirak, E., Segal, D., Assaraf, Y., and Reiter, Y. Targeting multidrug resistant tumor cells with a recombinant single-chain FV fragment directed to P-glycoprotein.: *Int. J. Cancer* 94: 864-872, 2001.
20. Hollo Z, Homolya L, Davis C W, Sarkadi B. Calcein accumulation as a fluorometric functional assay of the multidrug transporter. *Biochim Biophys Acta.* 1191:384-8, 1994.
21. Eva A, Robbins K C, Andersen P R, Srinivasan A, Tronick S R, Reddy E P, Ellmore N W, Galen A T, Lautenberger J A, Papas T S, Westin E H, Wong-Staal F, Gallo R C, Aaronson S A. Cellular genes analogous to retroviral onc genes are transcribed in human tumour cells. *Nature* 295:116-9, 1982.
22. Denkberg, G., Cohen, C J., Lev, A., Chames, P., Hoogenboom, H., and Reiter, Y. Direct visualization of distinct T cell epitopes derived from a melanoma tumor-associated antigen by using human recombinant antibodies with MHC-restricted T cell receptor-like specificity. *Proc. Natl. Acad. Sci. USA.* 99: 9421-9426, 2002.
23. Gupta R S, Siminovitch L. Mutants of CHO cells resistant to the protein synthesis inhibitors, cryptopleurine and tylocrebrine: genetic and biochemical evidence for common site of action of emetine, cryptopleurine, tylocrebine, and tubulosine. *Biochemistry* 16:3209-14, 1977.
24. Akiyama S, Fojo A, Hanover J A, Pastan I, and Gottesman M M Isolation and genetic characterization of human KB cell lines resistant to multiple drugs. *Somat Cell Mol Genet* 11: 117-26, 1985
25. Fojo A, Hamilton T C, Young R C, and Ozols R F. Multidrug resistance in ovarian cancer. *Cancer* 60:2075-80, 1987.
26. Sharma, R. C., Assaraf, Y. G., and Schimke, R. T. A phenotype conferring selective resistance to lipophilic antifolates in Chinese hamster ovary cells. *Cancer Res.* 51:2949-2959, 1991.
27. Schinkel, A H., The physiological function of drug-transporting P-glycoproteins. *Semin Can. Biol.* 8:161-170, 1997.
28. Chowdhury, P. S., & Pastan, I. Improving antibody affinity by mimicking somatic hypermutation in vitro. *Nat Biotechnol.* 17:568-72, 1999.
29. Forlani G. Bossi E, Ghirardelli R, Giovannardi S, Binda F, Bonadiman L, Ielmini L, Peres A. Mutation K448E in the external loop 5 of rat GABA transporter rGAT1 induces pH sensitivity and alters substrate interactions. *J Physiol.* 536:479-94, 2001
30. Kanner B I, Kavanaugh M P, Bendahan A. Molecular characterization of substrate-binding sites in the glutamate transporter family. *Biochem Soc Trans.* 29:707-10, 2001.
31. Loo T W, Clarke D M. Identification of residues in the drug-binding site of human P-glycoprotein using a thiol-reactive substrate. *J Biol. Chem.* 272:31945-8, 1997.
32. Loo T W, Bartlett M C, Clarke D M. Drug binding in human P-glycoprotein causes conformational changes in both nucleotide-binding domains. *J Biol Chem. In press* 2002.
33. Cattaneo A, and Biocca S. The selection of intracellular antibodies *Trends Biotechnol* 17:115-21, 1999.
34. Heike Y, Kasono K, Kunisaki C, Hama S, Saijo N, Tsuruo T, Kuntz D A, Rose D R, Curiel D T. Overcoming multi-drug resistance using an intracellular anti-mdr1 sFv. *Int J Cancer* 92:115-22, 2001.

What is claimed is:

1. A single chain Fv antibody comprising an antigen binding region capable of binding an extracellular portion of a P-glycoprotein, wherein said antigen binding region is encoded by a nucleic acid sequence as set forth by SEQ ID NO:2.

* * * * *